United States Patent
Hwang et al.

(10) Patent No.: US 10,654,848 B1
(45) Date of Patent: May 19, 2020

(54) NEUTROPHIL INFLAMMATION INHIBITOR AND USES THEREOF

(71) Applicant: Chang Gung University of Science and Technology, Taoyuan (TW)

(72) Inventors: Tsong-Long Hwang, New Taipei (TW); Yeh-Long Chen, Kaohsiung (TW); Cherng-Chyi Tzeng, Kaohsiung (TW); Chih-Hua Tseng, Tainan (TW)

(73) Assignees: Chang Gung University of Science and Technology, Taoyuan (TW); Chang Gung University, Taoyuan (TW); Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 16/185,017

(22) Filed: Nov. 9, 2018

(51) Int. Cl.
| C07D 407/02 | (2006.01) |
| C07D 471/04 | (2006.01) |
| A61P 11/00 | (2006.01) |
| C07D 498/04 | (2006.01) |
| A61P 17/06 | (2006.01) |

(52) U.S. Cl.
CPC ............ C07D 471/04 (2013.01); A61P 11/00 (2018.01); A61P 17/06 (2018.01); C07D 498/04 (2013.01)

(58) Field of Classification Search
CPC .................................................. C07D 471/02
See application file for complete search history.

(56) References Cited

U.S. PATENT DOCUMENTS

2018/0214426 A1* 8/2018 Chen .................... C07D 471/04

FOREIGN PATENT DOCUMENTS

WO WO-2016191576 A1 * 12/2016 ........... C07D 471/04

\* cited by examiner

*Primary Examiner* — Noble E Jarrell
*Assistant Examiner* — John S Kenyon

(57) ABSTRACT

Disclosed herein are compounds of formula (I), and pharmaceutical compositions comprising the same. The compounds of formula (I) are neutrophilic inflammation inhibitors, thus, they are useful for treatment and/or prophylaxis of inflammatory diseases and/or disorders associated with abnormal activation of neutrophils, such as ARDS, ALI, COPD, lung fibrosis, chronic bronchitis, pulmonary emphysema, α-1 anti-trypsin deficiency, cystic fibrosis, idiopathic pulmonary fibrosis, liver injury, steatohepatitis, liver fibrosis, damages caused by ischemia and reperfusion, myocardial infarction, shock, stroke, and organ transplantation, ulcerative cholitis, vasculitis, SLE, sepsis, SIRS, arthritis, psoriasis, atopic dermatitis, and inflammatory skin diseases.

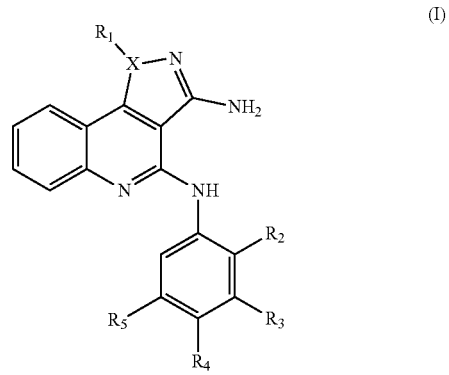

12 Claims, 4 Drawing Sheets
(3 of 4 Drawing Sheet(s) Filed in Color)

NEUTROPHIL INFLAMMATION INHIBITOR AND USES THEREOF

BACKGROUND OF THE INVENTION

1. Field of the Invention

The present disclosure in general relates to the field of inhibitors of neutrophilic inflammation, and their uses in the treatment or prophylaxis of neutrophil associated diseases and/or disorders.

2. Description of Related Art

Neutrophils are a class of white blood cells (leukocytes) that comprise an essential component of the host defense system against microbial invasion. In response to soluble inflammatory mediators released by cells at the site of injury, neutrophils emigrate into tissue from the bloodstream by crossing the blood vessel wall. At the site of injury, activated neutrophils kill foreign cells by phagocytosis and by the release of cytotoxic compounds, such as oxidants, proteases and cytokines. Despite their importance in fighting infection, neutrophils themselves can promote tissue damage. During an abnormal inflammatory response, neutrophils can cause significant tissue damage by releasing toxic substances at the vascular wall or in uninjured tissue. Alternatively, neutrophils that stick to the capillary wall may produce tissue damage by ischemia. Such abnormal inflammatory responses have been implicated in the pathogenesis of a variety of clinical disorders including, but not limiting to, acute respiratory distress syndrome (ARDS), acute lung injury (ALI), chronic obstructive pulmonary disease (COPD), lung fibrosis, liver injury, steatohepatitis, liver fibrosis, ischemia-reperfusion injury, myocardial infarction, shock, stroke, and organ transplantation, vasculitis, systemic lupus erythematosus (SLE), sepsis, systemic inflammatory response syndrome (SIRS), arthritis, psoriasis, atopic dermatitis, and inflammatory skin diseases.

Therefore, there is an unmet medical need for new therapeutic agents that may suppress abnormal activation of neutrophils, for the treatment and/or prophylaxis of inflammatory diseases and/or disorders associated therewith.

SUMMARY

The present disclosure is based on unexpected discovery that certain newly synthetic compounds are potent neutrophil inhibitors and may antagonize the inflammatory process resulted from abnormal activation of neutrophils, these compounds are thus useful as lead compounds for the development of medicaments for treating inflammatory diseases and/or disorders associated with abnormal activation of neutrophils, such as ARDS, ALI, COPD, lung fibrosis, chronic bronchitis, pulmonary emphysema, α-1 anti-trypsin deficiency, cystic fibrosis, idiopathic pulmonary fibrosis, liver injury, steatohepatitis, liver fibrosis, damages caused by ischemia and reperfusion, myocardial infarction, shock, stroke, and organ transplantation, ulcerative cholitis, vasculitis, SLE, sepsis, SIRS, arthritis, psoriasis, atopic dermatitis, and inflammatory skin diseases.

Accordingly, one aspect of the present disclosure is to provide a novel compound having the structure of formula (I), a salt, or a solvate thereof:

wherein,
X is N or O;
$R_1$ is H, alkyl or nil, in which $R_1$ is nil when X is O, and $R_1$ is H or alkyl when X is N;
$R_2$, $R_3$, $R_4$ and $R_5$ are independently H, hydroxyl, sulfhydryl, halogen, alkyl, haloalkyl, —$OR_6$, —$SR_6$, —(C=O)$R_6$, or —COOH;
$R_6$ is alkyl or haloalkyl.

According to one preferred embodiment of the present disclosure, in the formula (I), X is N; $R_1$ is methyl; $R_2$, $R_3$, and $R_5$ are independently H; and $R_4$ is hydroxyl.

The present disclosure also encompasses a pharmaceutical composition suitable for the treatment or prophylaxis of a disease and/or disorder resulted from abnormal activation of neutrophils. The pharmaceutical composition comprises the compound of formula (I), a salt, or a solvate thereof; and a pharmaceutically acceptable excipient.

Also encompasses in the present disclosure is a method for the treatment or prophylaxis of a subject having or suspected of having an inflammatory disease and/or disorder associated with abnormal activation of neutrophils. The method comprises the step of administering a therapeutically or prophylactically effective amount of the compound of formula (I), a salt or a solvate thereof to the subject, so as to ameliorate, mitigate and/or prevent the symptoms of the inflammatory disease and/or disorder associated with abnormal activation of neutrophils.

According to embodiments of the present disclosure, the inflammatory disease and/or disorder associated with abnormal activation of neutrophils is selected from the group consisting of ARDS, ALI, COPD, lung fibrosis, chronic bronchitis, pulmonary emphysema, α-1 anti-trypsin deficiency, cystic fibrosis, idiopathic pulmonary fibrosis, liver injury, steatohepatitis, liver fibrosis, damages caused by ischemia and reperfusion, myocardial infarction, shock, stroke, and organ transplantation, ulcerative cholitis, vasculitis, SLE, sepsis, SIRS, arthritis, psoriasis, atopic dermatitis, and inflammatory skin diseases.

According to one preferred embodiments of the present disclosure, the inflammatory disease and/or disorder is ARDS.

According to one preferred embodiment of the present disclosure, the inflammatory disease and/or disorder is ALI According to another preferred embodiments of the present disclosure, the inflammatory disease and/or disorder is psoriasis.

According to some embodiments of the present disclosure, the compound of formula (I) is administered to the subject in the amount of 0.001 to 100 mg/Kg.

According to preferred embodiments of the present disclosure, the subject is a human.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of the specification, illustrate various example systems, methods and other exemplified embodiments of various aspects of the invention. The present description will be better understood from the following detailed description read in light of the accompanying drawings, where, FIG. 1 illustrate the effect of compound HKI-4971 on imiquimod-induced psoriasis in mice. (A) Presentation of phenotype of mice from IMQ group (left) and HKI4971 group (right). (B) Microscopic presentation of skin from the IMQ group mouse. (C) Microscopic presentation of skin from the HKI4971 group mouse. Scale bar=1 mm.

DETAILED DESCRIPTION OF THE INVENTION

The detailed description provided below in connection with the appended drawings is intended as a description of the present disclosure and is not intended to represent the only forms in which the present disclosure may be constructed or utilized.

1. Definitions

The term "alkyl" includes substituted and unsubstituted straight, branched and cyclic alkyl groups. Unless otherwise specified, each instance of an alkyl group is independently optionally substituted, i.e., unsubstituted (an "unsubstituted alkyl") or substituted (a "substituted alkyl") with one or more substituents. The term "substituted," when used to describe a chemical structure or moiety, refers to a derivative of that structure or moiety wherein one or more of its hydrogen atoms is substituted with one or more of: halo, haloalkyl, or hydroxyl. In certain embodiments, the alkyl group is unsubstituted alkyl, particularly, alkyl having 1-6 carbon atoms (or lower alkyl), such as methyl, ethyl, propyl, butyl, and the like. In certain embodiments, the alkyl group is substituted with at least one substitutents (e.g., haloalkyl).

The term "halo" or "halogen" refers to fluorine (fluoro, —F), chlorine (chloro, —Cl), bromine (bromo, —Br), or iodine (iodo, —I).

The term "haloalkyl" denotes an alkyl group, as defined above, having one, two, three, four, five, six, or more halogen atoms attached thereto. Haloalkyl includes fluoroalkyl, chloroalkyl, bromoalkyl, and iodoalkyl. "Fluoroalkyl" refers to an alkyl group having one, two, three, four, five, six, or more fluorine atoms attached thereto. A haloalkyl group may include more than one type of halogen atoms. For example, fluoroalkyl includes an alkyl group having one or more fluorine atoms and one or more chlorine atoms. A haloalkyl group may be substituted with one or more substituents that are not halogen atoms.

The term "alkoxy" refers to a moiety of the formula: —OR', wherein R' is an optionally substituted alkyl group described herein.

The present disclosure is not intended to be limited in any manner by the above exemplary listing of substituents.

The term "salt" refers to a pharmaceutically acceptable salt which is, within the scope of sound medical judgment, suitable for use in contact with the tissues of humans and lower animals without undue toxicity, irritation, allergic response and the like, and is commensurate with a reasonable benefit/risk ratio. Pharmaceutically acceptable salts are well known in the art. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.$0.5H_2O$)), and polyhydrates (x is a number greater than 1, e.g., dihydrates (R.$2H_2O$) and hexahydrates (R.$6H_2O$)).

The term "pharmaceutically acceptable excipient" refers to compounds that are compatible with other ingredients in a pharmaceutical composition and would not endanger the subject after administering.

Unless otherwise indicated, the term "effective amount" as referred to herein designate the quantity of a compound which is sufficient to yield a desired response. For therapeutic purposes, the effective amount is also one in which any toxic or detrimental effects of the compound are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the compound of formula (I) the present disclosure), such as molar concentration, mass concentration, volume concentration, molality, mole fraction, mass fraction and mixing ratio. Further, persons having ordinary skills in the related art could calculate the human equivalent dose (HED) for the medicament (such as the compound of the present disclosure) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

The term "subject" or "patient" is used interchangeably herein and is intended to mean a mammal including the human species that is treatable by the compound of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Neutrophil Inhibitors

Inventors of the present disclosure unexpectedly identify certain synthetic compounds are potent inhibitors of neutrophilic inflammation. It was found that the compounds of the present disclosure may antagonize the inflammatory process caused by abnormal activation of neutrophils, these compounds are thus useful as lead compounds for the development of medicaments for treating inflammatory diseases and/or disorders associated therewith.

The compounds as described herein can have the structure of formula (I), which is described herein, and pharmaceutically acceptable salts or solvates thereof.

(I)

In some embodiments, they can be salts, solvates, or hydrates of formula (I).

In formula (I), X can be N or O. Alternatively or in addition, $R_1$ is H, alkyl or nil, in which $R_1$ is nil when X is O, and $R_1$ is H or alkyl when X is N. Further, $R_1$ can be substituted or unsubstituted. In certain embodiments, $R_1$ is methyl.

Alternatively or in addition, $R_2$, $R_3$, $R_4$ and $R_5$ are independently H, hydroxyl, sulfhydryl, halogen, alkyl, haloalkyl, —$OR_6$, —$SR_6$, —(C=O)$R_6$, or —COOH; and $R_6$ is alkyl or haloalkyl.

In certain embodiment, the compound of formula (I) can be compound 3, in which X is N, $R_1$ is methyl, and $R_2$, $R_3$, $R_4$ and $R_5$ are independently H.

In certain embodiment, the compound of formula (I) can be compound 4, in which X is N, $R_1$ is methyl, and $R_2$, $R_3$ and $R_5$ are independently H, and $R_4$ is a fluoro.

In certain embodiment, the compound of formula (I) can be compound 7, in which X is N, $R_1$ is methyl, $R_4$ is —$OR_6$, with $R_6$ being methyl; and $R_2$, $R_3$ and $R_5$ are independently H.

In certain embodiment, the compound of formula (I) can be compound 8, in which X is N, $R_1$ is methyl, $R_2$ is H, and $R_3$, $R_4$, and $R_5$ are independently —$OR_6$, with $R_6$ being methyl.

In certain embodiment, the compound of formula (I) can be compound 10, in which X is N, $R_1$ is methyl, $R_4$ is —(C=O)$R_6$, with $R_6$ being methyl, and $R_2$, $R_3$ and $R_5$ are independently H.

In certain embodiment, the compound of formula (I) can be compound 11, in which X is N, $R_1$ is methyl, $R_2$ is hydroxyl, and $R_3$, $R_4$ and $R_5$ are independently H.

In certain embodiment, the compound of formula (I) can be compound 12, in which X is N, $R_1$ is methyl, $R_3$ is hydroxyl; while $R_2$, $R_4$ and $R_5$ are independently H.

In certain embodiment, the compound of formula (I) can be compound 13, in which X is N, $R_1$ is methyl, $R_4$ is hydroxyl, and $R_2$, $R_3$ and $R_5$ are independently H.

In certain embodiment, the compound of formula (I) can be compound 15, in which X is N, $R_1$ is methyl, $R_2$, $R_3$, and $R_5$ are independently H, and $R_4$ is carboxyl.

In certain embodiment, the compound of formula (I) can be compound 16, in which X is N, $R_1$ is methyl, $R_2$ is sulfhydryl, and $R_3$, $R_4$ and $R_5$ are independently H.

In certain embodiment, the compound of formula (I) can be compound 17, in which X is N, $R_1$ is methyl, $R_4$ is a chloro, and $R_2$, $R_3$ and $R_5$ are independently H.

In certain embodiment, the compound of formula (I) can be compound 28, in which X is O, $R_2$ is hydroxy, and $R_3$, $R_4$ and $R_5$ are independently H.

In certain embodiment, the compound of formula (I) can be compound 30, in which X is O, $R_4$ is alkyl substituted with three fluoro (i.e., trifluoromethyl (—$CF_3$)), and $R_2$, $R_3$ and $R_5$ are independently H.

The compounds of the present disclosure may selectively inhibit the activities of neutrophils, which include inhibition of one or more of the following activities by neutrophils: release of superoxide anion, release of reactive oxygen species, release of myeloperoxidase, release of elastase, neutrophil aggregation, adhesion to plastic surfaces, adhesion to vascular endothelial cells, chemotaxis, and transmigration across a monolayer of endothelial cells. In some embodiments, the compounds of the present disclosure may inhibit superoxide anion generated from formyl-L-methionyl-L-leucyl-L-phenylalanine (fMLF)-activated neutrophils. In other embodiments, the compounds of the present disclosure may inhibit release of elastase from fMLF-activated neutrophils.

The inhibition of the superoxide anion generation by a compound of the present disclosure may be measured by the half maximal inhibitory concentrations ($IC_{50}$) value of a compound of the present disclosure when the compound of formula (I), or a salt or a solvate thereof, is contacted, directly or indirectly, with the fMLF-activated neutrophils. In certain embodiments, the $IC_{50}$ value of a compound of the present disclosure is at most about 4 nM, at most about 0.5 µM, at most about 5 µM, at most about 8 µM, at most about 10 µM for the suppression of superoxide anion generation in fMLF-activated neutrophils. In certain embodiments, the $IC_{50}$ value of a compound of the present disclosure is at least about 30 nM, at least about 2 µM, at least about 5 µM, at least about 10 µM for the suppression of elastase release fMLF-activated neutrophils.

3. Method of Preparing the Compounds

Any of the compounds described herein can be prepared by routine methods known in the art or by methods described in working examples.

In general, a compound as described herein (e.g., a compound of Formula (I), can be prepared by treating (e.g., contacting) a pyrazolo[4,3-c]quinoline (i.e., compound 2a or 2b of Example 1), with a substituted aniline (e.g., 2-methoxy aniline, 4-fluoroaniline and etc.). The reaction (e.g., the step of contacting) can be conducted in an aprotic solvent, such as dimethyl sulfoxide (DMSO), dimethylformamide (DMF), N-methyl-2-pyrrolidone (NMP), dichloromethane (DCM), tetrahydrofuran (THF), acetone, ethanol, propanol and the like. The reaction is monitored by thin layer chromatography (TLC) or high performance liquid chromatography (HPLC), and the product is identified by MS and NMR spectra.

4. Pharmaceutical Composition and Kits

This disclosure also encompasses pharmaceutical compositions for the treatment or prophylaxis of an inflammatory disease and/or disorder, particularly the one that is associated with abnormal activation of neutrophils. The pharmaceutical composition comprises a therapeutically or prophylactic effective amount of the compound of formula (I) of the present disclosure (e.g., compound 13), a slat or a solvate thereof, and a pharmaceutical acceptable excipient.

The compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Examples of dosage forms include, but are not limited to: tablets; caplets; capsules, such as soft elastic gelatin capsules; cachets; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin or β-cyclodextrin), and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:corn oil).

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

4.1 Oral Dosage Forms

Pharmaceutical compositions of the present invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., Remington's Pharmaceutical Sciences, 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

4.2 Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: water; aqueous vehicles such as, but not limited to, sodium chloride solution, Ringer's solution, and Dextrose; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

4.3 Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 18th eds., Mack Publishing, Easton Pa. (1990). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition

4.4 Kits

Also encompasses within the present disclosure is an article of manufacture or "kit," containing materials useful for the treatment or prophylaxis of a disease and/or disorder associated with neutrophils in a subject.

In one embodiment, the kit comprises a container comprising the compound of the present disclosure. The kit is suitable for the treatment or prophylaxis of an inflammatory disease and/or disorder, particularly the one that is associated with abnormal activation of neutrophils, such as chronic obstructive pulmonary disease (COPD), chronic bronchitis (CB), pulmonary emphysema, α-1 anti-trypsin deficiency, cystic fibrosis, idiopathic pulmonary fibrosis, adult respiratory distress syndrome, psoriasis, rheumatoid arthritis, ulcerative cholitis, sepsis, and damages caused by ischemia and reperfusion. Suitable containers include, for example, bottles, vials, syringes, blister pack, and etc. The container may be formed from a variety of materials such as glass, or plastic. The container may hold a compound of the present disclosure or a pharmaceutical formulation thereof, in an amount effective for the treatment or prophylaxis of the inflammatory disease and/or disorder associated with abnormal activation of neutrophils, and may have a sterile access port, for example, the container may be an intravenous solution bag or a vail having a stopper pierceable by a hypodermic injection needle). The kit may further comprise a label or package insert on or associated with the container. The label or package insert indicates that the composition is used for treating condition of choice. Alternatively or additionally, the kit may further comprise a second container comprising a pharmaceutically acceptable buffer, such as a phosphate-buffered saline, Ringer's solution or dextrose solution. It may further include other materials desirable from a commercial and user standpoint, including other buffers, diluents, filters, needles, and syringes.

The kit may further include directions for the administration of the compound of the present invention and, if present, the second formulation for treating or preventing the inflammatory disease and/or disorder associated with abnormal activation of neutrophils. For example, if the kit comprises a first composition comprising the compound of the present disclosure, and a second pharmaceutical formulation, the kit may further include directions for the simultaneous, sequential, or separate administration of the first and second pharmaceutical compositions to a patient in need thereof.

In another embodiment, the kits are suitable for the delivery of solid oral forms of a compound of the present disclosure, such a kit includes, for example, a number of unit dosages. Such kits include card having the dosages oriented in the order of their intended use. An example of such kit is a "blister pack." Blister packs are well known in the packaging industry and are widely used for packaging pharmaceutical unit dosage forms. If desired, an aid may be provided, for example, in the form of numbers, letters, or other markings or with a calendar insert, designating the days in the treatment schedule in which the dosage can be administered.

According to one embodiment, the Kit may include, at least, (a) a first container containing the present compound of formula (I); and optionally, (b) a second container containing a second therapeutic agent that is any of a known anti-inflammatory agent, an anti-biotic, an anti-neoplasm agent, or a cardiovascular drug; and (c) a legend associated with the kit for instructing a user how to use the kit. The legend may be in a form of pamphlet, tape, CD, VCD or DVD.

5. Methods of Treatment

As the compounds of the present disclosure may antagonize the activation of neutrophils signaling, thus they are useful as lead compounds for the development of medicaments for treating inflammatory diseases and/or disorders, particularly those associated with abnormal activation of neutrophils. The present invention thus is directed to the therapeutic use of the compound of formula (I) for the treatment or prophylaxis of neutrophils associated diseases and/or disorders, such as ARDS, ALI, COPD, lung fibrosis, chronic bronchitis, pulmonary emphysema, α-1 anti-trypsin deficiency, cystic fibrosis, idiopathic pulmonary fibrosis, liver injury, steatohepatitis, liver fibrosis, damages caused by ischemia and reperfusion, myocardial infarction, shock, stroke, and organ transplantation, ulcerative cholitis, vasculitis, SLE, sepsis, SIRS, arthritis, psoriasis, atopic dermatitis, and inflammatory skin diseases.

The present invention thus encompasses a method for the treatment or prophylaxis of a subject having or suspected of having an inflammatory disease and/or disorder associated with abnormal activation of neutrophils. The method comprises the step of administering a therapeutically or prophylactically effective amount of the compound of formula (I), a salt or a solvate thereof to the subject, so as to ameliorates, mitigates and/or prevents the symptoms of the inflammatory disease and/or disorder associated with the abnormal activation of neutrophils.

The compound of formula (I) of the present disclosure may be synthesized in accordance with process set forth in the working examples of the present disclosure.

According to embodiments of the present disclosure, the inflammatory disease and/or disorder associated with abnormal activation of neutrophils may be ARDS, ALI, COPD, lung fibrosis, chronic bronchitis, pulmonary emphysema, α-1 anti-trypsin deficiency, cystic fibrosis, idiopathic pulmonary fibrosis, liver injury, steatohepatitis, liver fibrosis, damages caused by ischemia and reperfusion, myocardial infarction, shock, stroke, and organ transplantation, ulcerative cholitis, vasculitis, SLE, sepsis, SIRS, arthritis, psoriasis, atopic dermatitis, or inflammatory skin diseases.

Other existing treatments of such disease and/or disorders may also be used along with the present treatment. Accordingly, the present invention also encompasses administering another therapeutic agent conventionally used to treat inflammatory diseases and/or disorders associated with the activation of neutrophils, before, together with, or after the administration of the compound of formula (I). The therapeutic agent conventionally used to treat inflammatory diseases and/or disorders may be a known an anti-inflammatory agent (e.g., steroid), an anti-biotic (e.g., penicillin), an anti-neoplasm agent, or a cardiovascular drug. For example, in the case of treating ARDS, in addition to administering the compound of formula (I), a salt or solvate thereof to the asthma patient, the present method may further include administering any agent known to attenuate, reduce or alleviate the level of bronchoconstriction or bronchospasm associated with ARDS.

According to embodiments of the present disclosure, the compound of formula (I) may be administered to the subject in the amount of about 0.001-100 mg/Kg, such as 0.001, 0.002, 0.003, 0.004, 0.005, 0.006, 0.007, 0.008, 0.009, 0.01, 0.05, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 mg/Kg; preferably in the amount of about 0.01-90 mg/Kg, such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and 90 mg/Kg; more preferably in the amount of about 0.11-80 mg/Kg, such as 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, and 80 mg/Kg.

The amount, route of administration and dosing schedule of the compound of formula (I), a salt, a solvate thereof, will depend upon factors such as the specific indication to be treated, prevented, or managed, and the age, sex and condition of the patient. The roles played by such factors are well known in the art, and may be accommodated by routine experimentation.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods
Neutrophil Preparation

Human neutrophils were obtained in lipopolysaccharide-free conditions by means of dextran sedimentation and Ficoll centrifugation.

Animals

Male BALB/c mice aged 7-8 weeks were purchased from BioLASCO (Taipei, Taiwan) and maintained in a room with 12 hr light/dark cycles. Standard laboratory chow and water were available ad libitum. All animal experimental procedures were performed in accordance with guidelines and approved by the Institutional Animal Care and Use Committee of Chang Gung University.

Measurement of $O_2^{\bullet-}$ Production $O_2^{\bullet-}$ production was determined based on the SOD-inhibitable reduction of ferricytochrome c. Briefly, neutrophils ($6\times10^5$/mL) were treated with a candidate compound at 37° C. at various concentrations (0.001 to 10 µM) for 5 min after being supplementing with 0.5 mg/mL ferricytochrome c and 1 mM $Ca^{2+}$. Cells were then activated with fMLF (0.1 µM) for 10 min in the pre-process of cytochalasin B (CB, 1 µg/mL) for 3 min. Changes in absorbance with the reduction of ferricytochrome c at 550 nm were continuously monitored in a double-beam, six-cell positioner spectrophotometer with constant stirring (Hitachi U-3010, Tokyo, Japan). Calculations were based on the differences in the reactions with and without SOD (100 U $ml^{-1}$) divided by the extinction coefficient for the reduction of ferricytochrome c (E=21.1 $mM^{-1}$/10 mm).

Measurement of Elastase Release

Methoxysuccinyl-Ala-Ala-Pro-Val-p-nitroanilide was employed as the elastase substrate for the determination of elastase release. Briefly, after supplementation with Methoxysuccinyl-Ala-Ala-Pro-Val-p-nitroanilide (100 µM), neutrophils ($6\times10^5$/mL) were equilibrated at 37° C. for 2 min and incubated with a candidate compound at various concentrations for 5 min. Cells were then activated with fMLF (0.1 µM) for 10 min in the pre-process of CB (0.5 µg/mL) for 3 min, and changes in absorbance at 405 nm were continuously monitored to evaluate elastase release. Results are expressed as the percentage of elastase release in the drug-free control group, DMSO.

Cell Viability Test

Cytotoxicity of a candidate compound towards neutrophils was evaluated by measuring the level of lactate dehydrogenase (LDH) using a commercial kit (Promega). LDH is a cytosolic enzyme that is released only when cell membrane is disrupted (i.e., cell death), thus may be used as an indicator of cell viability. The kit measures a color change at (Xmax=450 nm) when LDH reduces NAD to NADH. Cytotoxicity was expressed as the percent LDH activity obtained in cell-free medium compared to the total LDH activity. Total LDH activity was determined by lysing cells with 0.1% Triton X-100 for 30 min at 37° C.

LPS-Induced ALI Model

Mice were pre-treated with a candidate compound (e.g., HKI-4971), which was dissolved in 50 μl saline solution containing 10% DMSO and 20% Kolliphor EL (Sigma-Aldrich, USA), by intravenous injection. One hour after the administration, mice were anaesthetized with Zoletil 50 (30 mg/kg) and xylazine (6 mg/kg) and challenged with an intratracheal aerosol spray of 50 μg of LPS (*Escherichia coli* 0111:B4; Sigma-Aldrich, USA) dissolved in 40 μl normal saline. Mice without LPS spray were injected with saline as the controls. At 5 h after inoculation, mice were sacrificed by cervical dislocation and lungs were removed. The left lobe of lung was fixed in 10% buffered neutral formalin for histological examination and the right four lobes were assayed for MPO activity.

Myeloperoxidase (MPO) Activity Assay

Lung tissues were homogenized in PBS (50 Mm, pH 6.0) containing 0.5% (w/v) hexadecyltrimethylammonium bromide (HETAB) (Sigma-Aldrich, USA) by using the MagNA Lyser Instrument (Roche, Germany), and was further centrifuged at 12,000×g for 20 min at 4° C. to remove the insoluble material. The peroxidase activity was measured as the oxidation of o-Dianisidine dihydrochloride (Sigma-Aldrich, USA). Briefly, the homogenate were added with 0.2 mg/ml o-Dianisidine dihydrochloride containing 0.001% $H_2O_2$ and then incubated at room temperature for 10 min. The absorption was determined spectrophotometrically at 405 nm. MPO activity was normalized to protein concentration based on the Bradford method (Bio-Rad, USA).

Imiquimod-Induced Psoriasis-Like Skin Inflammation in Mice

Male BALB/c mice aged 7-8 weeks were used for the development of the imiquimod-induced psoriatic-like plaque model. The dorsal skin of the mice were shaved and received a daily topical dose of 62.5 mg of 5% imiquimod (IMQ) cream (Aldara, MEDA Pharma, Sweden) with or without a test compound (e.g., HKI-4971) treatment by intraperitoneal injection for 7 consecutive days.

Histopathology and Immunohistochemistry

Tissue samples were fixed in 10% neutral buffered formalin and embedding in paraffin blocks. Sections of the samples were prepared at 5 μm thickness and stained with hematoxylin and eosin (H&E). For immunohistochemistry staining, the sections were incubated with primary antibodies against Ly6g, MPO, and ki67 then the secondary antibody was applied for the detection of the primary antibody according to the manufacturer's instructions of the SuperPicture Polymer Detection Kit (Thermo Fisher, USA). Finally, the section slides were subsequently stained with DAB chromogen and counterstained with hematoxylin.

Statistical Analysis

Results are expressed as the mean±standard error of the mean (SEM), and comparisons were made using Student's t-test. A probability of 0.05 or less was considered significant. The software SigmaPlot was used for the statistical analysis.

Example 1 Production and Characterization of Compound of Formula (I)

1.1 Production of Compound of Formula (I)

In general, the compound of formula (I) was synthesized in accordance with the procedures described in Scheme I.

Scheme I

The compound of formula (I)

| Compound # and name | X | $R_1$ | $R_2$ | $R_3$ | $R_4$ | $R_5$ |
|---|---|---|---|---|---|---|
| 3 HKI-4961 | N | $CH_3$ | H | H | H | H |
| 4 HKI-4962 | N | $CH_3$ | H | H | F | H |
| 5 HKI-4966 | N | $CH_3$ | $OCH_3$ | H | H | H |
| 6 HKI-4965 | N | $CH_3$ | H | $OCH_3$ | H | H |
| 7 HKI-4964 | N | $CH_3$ | H | H | $OCH_3$ | H |
| 8 HKI-4963 | N | $CH_3$ | H | $OCH_3$ | $OCH_3$ | $OCH_3$ |
| 9 HKI-4967 | N | $CH_3$ | H | H | $SCH_3$ | H |
| 10 HKI-4968 | N | $CH_3$ | H | H | —(C=O)$CH_3$ | H |
| 11 HKI-4973 | N | $CH_3$ | OH | H | H | H |
| 12 HKI-4972 | N | $CH_3$ | H | OH | H | H |
| 13 HKI-4971 | N | $CH_3$ | H | H | OH | H |
| 14 HKI-4974 | N | $CH_3$ | H | H | $CF_3$ | H |
| 15 HKI-4970 | N | $CH_3$ | H | H | COOH | H |
| 16 HKI-4975 | N | $CH_3$ | SH | H | H | H |
| 17 TCH-30o | N | $CH_3$ | H | H | Cl | H |
| 18 TCH-30p | N | $CH_3$ | H | H | $CH_3$ | H |
| 19 HKI-4978 | O | Nil | H | H | H | H |
| 20 HKI-4979 | O | Nil | H | H | F | H |
| 21 HKI-4983 | O | Nil | $OCH_3$ | H | H | H |
| 22 HKI-4982 | O | Nil | H | $OCH_3$ | H | H |
| 23 HKI-4981 | O | Nil | H | H | $OCH_3$ | H |
| 24 HKI-4980 | O | Nil | H | $OCH_3$ | $OCH_3$ | $OCH_3$ |
| 25 HKI-4984 | O | Nil | H | H | $SCH_3$ | H |
| 26 HKI-4986 | O | Nil | H | —(C=O)$CH_3$ | H | H |
| 27 HKI-4987 | O | Nil | H | H | —(C=O)$CH_3$ | H |
| 28 HKI-4990 | O | Nil | OH | H | H | H |
| 29 HKI-4988 | O | Nil | H | H | OH | H |

-continued

| Compound # and name | X | $R_1$ | $R_2$ | $R_3$ | $R_4$ | $R_5$ |
|---|---|---|---|---|---|---|
| 30 HKI-4991 | O | Nil | H | H | $CF_3$ | H |
| 31 HKI-4985 | O | Nil | H | H | COOH | H |
| 32 TCH-30q | O | Nil | H | H | Cl | H |
| 33 TCH-30r | O | Nil | H | H | $CH_3$ | H |

4-Chloro-1-methyl-1H-pyrazolo[4,3-c]quinolin-3-amine (compound 2a; X=N, $R_1$=$CH_3$)

A mixture of 2,4-dichloro-3-cyanoquinoline (5.48 g, 24.6 mmol) and methylhydrazine (2.21 g, 48.0 mmol) in EtOH (100 mL) was refluxed for 2 h (TLC monitoring). The reaction mixture was concentrated in vacuo and the precipitate was collected by filtration, washed with EtOH, $H_2O$ and dried to yield pale yellow solid. The crude product was recrystallized with EtOH to give compound 2a (4.23 g, 74%).

$^1$H-NMR (200 MHz, DMSO-$d_6$): δ 7.65-7.78 (m, 2H, Ar—H), 7.92-7.96 (m, 1H, Ar—H), 7.39-7.44 (m, 1H, Ar—H).

4-Chloroisoxazolo[4,5-c]quinolin-3-amine (compound 2b; X=O, $R_1$=H)

A mixture of 2,4-dichloro-3-cyanoquinoline (1.12 g, 5 mmol), hydroxylamine hydrochloride (1.03 g, 15 mmol), and $K_2CO_3$ (2.07 g, 15 mmol) in EtOH (30 mL) was refluxed for 1 hr (TLC monitoring). The reaction mixture was concentrated in vacuo followed by the addition of $H_2O$ (100 mL). Precipitate was collected by filtration, washed with $H_2O$ and dried to yield yellow solid. The crude product was recrystallized with MeOH to give compound 2b (0.71 g, 65%).

Mp.: 194-196° C.

$^1$H-NMR (400 MHz, DMSO-$d_6$): 7.52-7.60 (m, 1H, Ar—H), 7.73-7.78 (m, 2H, Ar—H), 8.06 (d, 1H, J=7.6 Hz, Ar—H), 8.72 (br s, 2H, $1H_2$).

General Procedure for the synthesis of 4-substituted-anilino-1-methyl-1H-pyrazolo[4,3-c]quinolin-3-amine (compounds 3-18) and 4-substituted-anilinoisoxazolo[4,5-c]quinolin-3-amine (Compounds 19-33)

A mixture of 2a or 2b (2 mmol) and appropriate substituted-aniline (4 mmol) in DMF (25 mL) was refluxed with stirring for 2-5 hrs (by TLC monitoring). The mixture was then cooled and evaporated in vacuo to give a residue which was treated with $H_2O$ (50 mL). The precipitate thus collected was washed with $H_2O$ and then dried to give a crude solid, which was recrystallized from EtOH.

Each compound was identified by: thin layer chromatography (TLC) (pre-coated (0.2 mm) silica gel 60 $F_{254}$ plates from EM Laboratories, Inc) detected by UV light (254 nm); melting point (Electrothermal IA9100 digital melting-point apparatus; uncorrected); and $^1$H and $^{13}$C NMR spectra (Varian-Unity-400 spectrometer at 400 and 100 MHz or Varian-Gemini-200 spectrometer at 200 and 50 MHz, chemical shifts δ in ppm with $SiMe_4$ as an internal standard (=0 ppm), coupling constants J in Hz). Elemental analyses were carried out on a Heraeus CHN—O-Rapid elemental analyzer, and results were within ±0.4% of calculated values.

4-Anilino-1-methyl-1H-pyrazolo[4,3-c]quinolin-3-amine (compound 3, HKI-4961)

Yield 40%. M.p.: 186-187° C. (EtOH). $^1$H-NMR (400 MHz, DMSO-$d_6$): δ 4.19 (s, 3H, N$CH_3$), 5.58 (br s, 2H, $NH_2$), 6.99-7.03 (m, 1H, Ar—H), 7.33-7.37 (m, 3H, Ar—H), 7.52-7.56 (m, 1H, Ar—H), 7.67-7.70 (m, 1H, Ar—H), 7.95-7.97 (m, 2H, Ar—H), 8.22-8.24 (m, 1H, Ar—H), 8.25 (br s, 1H, NH). $^{13}$C-NMR (100 MHz, DMSO-$d_6$): δ 39.18, 99.13, 114.49, 119.93 (2C), 121.71, 121.96, 122.46, 126.96, 128.45 (2C), 128.51, 140.52, 140.67, 146.07, 147.29, 148.95. Anal. calcd for $C_{17}H_5N_5$: C, 70.57; H, 5.23; N, 24.21. found: C, 70.20; H, 5.24; N, 24.14.

4-(4-Fluoroanilino)-1-methyl-1H-pyrazolo[4,3-c]quinolin-3-amine (Compound 4, HKI-4962)

Yield 62%. M.p.: 218-219° C. (EtOH). $^1$H-NMR (400 MHz, DMSO-$d_6$): δ 4.19 (s, 3H, N$CH_3$), 5.90 (br s, 2H, $NH_2$), 7.24-7.28 (m, 2H, Ar—H), 7.37-7.41 (m, 1H, Ar—H), 7.55-7.59 (m, 1H, Ar—H), 7.72-7.74 (m, 1H, Ar—H), 7.84-7.87 (m, 2H, Ar—H), 8.24-8.26 (m, 1H, Ar—H), 9.26 (br s, 1H, NH). $^{13}$C-NMR (100 MHz, DMSO-$d_6$): δ 39.35, 97.75, 113.74, 115.39, 115.61, 112.36 (2C), 123.37, 123.84, 129.14, 135.390, 140.05, 142.33, 148.59, 157.37, 159.74. Anal. calcd for $C_{17}H_{14}FN_5$·3HCl: C, 64.14; H, 4.53; N, 22.00. found: C, 63.87; H, 4.73; N, 21.77.

4-(2-Methoxyanilino)-1-methyl-1H-pyrazolo[4,3-c]quinolin-3-amine (Compound 5, HKI-4966)

Yield 74%. M.p.: 229-230° C. (EtOH). $^1$H-NMR (400 MHz, DMSO-$d_6$): δ 3.90 (s, 3H, O$CH_3$), 4.21 (s, 3H, N$CH_3$), 5.21 (br s, 2H, $NH_2$), 6.98-7.08 (m, 3H, Ar—H), 7.32-7.36 (m, 1H, Ar—H), 7.53-7.57 (m, 1H, Ar—H), 7.73-7.75 (m, 1H, Ar—H), 8.22-8.24 (m, 1H, Ar—H), 8.69 (br s, 1H, NH), 8.99-8.02 (m, 1H, Ar—H). $^{13}$C-NMR (100 MHz, DMSO-$d_6$): δ 39.11, 56.04, 100.52, 110.55, 114.44, 119.16, 120.50, 121.46, 121.96, 122.43, 127.12, 128.50, 129.78, 140.20, 146.35, 147.28, 148.05, 149.12. Anal. calcd for $C_{18}H_{17}FN_5O$: C, 67.70; H, 5.37, N, 21.93. found: C, 67.37; H, 5.39; N, 21.85.

4-(3-Methoxyanilino)-1-methyl-1H-pyrazolo[4,3-c]quinolin-3-amine (Compound 6, HKI-4965)

Yield 79%. M.p.: 284-286° C. (EtOH). $^1$H-NMR (400 MHz, DMSO-$d_6$): δ 3.80 (s, 3H, O$CH_3$), 4.19 (s, 3H, N$CH_3$), 5.58 (br s, 2H, $NH_2$), 6.58-6.60 (m, 1H, Ar—H), 7.22-7.26 (m, 1H, Ar—H), 7.32-7.42 (m, 2H, Ar—H), 7.53-7.75 (m, 1H, Ar—H), 7.69-7.71 (m, 1H, Ar—H), 7.88 (br s, 1H, NH), 8.23-8.26 (m, 2H, Ar—H). $^{13}$C-NMR (100 MHz, DMSO-$d_6$): δ 39.17, 54.93, 99.19, 105.43, 107.30, 112.12, 114.45, 121.97, 122.57, 126.97, 128.56, 129.11, 140.48, 141.86, 145.95, 147.24, 148.88, 159.49. Anal. calcd for $C_{18}H_{17}N_5O$·0.4HCl: C, 64.72; H, 5.26, N, 20.97. found: C, 64.96; H, 5.29; N, 21.08.

4-(4-Methoxyanilino)-1-methyl-1H-pyrazolo[4,3-c]quinolin-3-amine (Compound 7, HKI-4964)

Yield 62%. M.p.: 193-194° C. (EtOH). $^1$H-NMR (400 MHz, DMSO-$d_6$): δ 3.82 (s, 3H, O$CH_3$), 4.20 (s, 3H, N$CH_3$), 6.30 (br s, 2H, $NH_2$), 7.06-7.08 (m, 2H, Ar—H), 7.43-7.47 (m, 1H, Ar—H), 7.59-7.63 (m, 3H, Ar—H), 7.81-7.83 (m, 1H, Ar—H), 8.26-8.28 (m, 1H, Ar—H), 9.74 (br s, 1H, NH). $^{13}$C-NMR (100 MHz, DMSO-$d_6$): δ 39.58, 55.37, 96.37, 112.90, 114.71 (2C), 121.28, 122.79, 124.23, 125.78, 129.59, 129.82, 138.43, 139.55, 148.50, 149.88, 157.43. Anal. calcd for $C_{18}H_{17}N_5O.0.5HCl$: C, 64.02; H, 5.23; N, 20.74. found: C, 64.13; H, 5.42; N, 20.69.

4-(3,4,5-Trimethoxyanilino)-1-methyl-1H-pyrazolo[4,3-c]quinolin-3-amine (Compound 8, HKI-4963)

Yield 63%. M.p.: 219-220° C. (EtOH). $^1$H-NMR (400 MHz, DMSO-d$_6$): δ 3.68 (s, 3H, OCH$_3$), 3.82 (s, 6H, OCH$_3$), 4.19 (s, 3H, NCH$_3$), 5.75 (br s, 2H, NH$_2$), 7.38 (m, 3H, Ar—H), 7.56-7.60 (m, 1H, Ar—H), 7.72-7.76 (m, 1H, Ar—H), 8.24-8.26 (m, 1H, Ar—H). $^{13}$C-NMR (100 MHz, DMSO-d$_6$): δ 39.29, 55.79 (2C), 60.12, 98.54, 113.92, 122.24, 122.97, 123.13, 127.10, 129.00, 140.11, 148.59, 152.85. Anal. calcd for $C_{20}H_{21}N_5O_3.0.5HCl$: C, 60.39; H, 5.46, N, 17.61. found: C, 60.08; H, 5.57; N, 17.36.

1-Methyl-4-(4-methylthioanilino)-1H-pyrazolo[4,3-c]quinolin-3-amine (Compound 9, HKI-4967)

Yield 84%. M.p.: 233-235° C. (EtOH). $^1$H-NMR (400 MHz, DMSO-d$_6$): δ 2.48 (s, 3H, SCH$_3$), 4.18 (s, 3H, NCH$_3$), 5.71 (br s, 2H, NH$_2$), 7.29-7.37 (m, 3H, Ar—H), 7.53-7.57 (m, 1H, Ar—H), 7.69-7.71 (m, 1H, Ar—H), 7.86-7.88 (m, 2H, Ar—H), 8.22-8.24 (m, 1H, Ar—H). $^{13}$C-NMR (100 MHz, DMSO-d$_6$): δ 15.88, 39.22, 98.58, 114.15, 121.42, 122.10 (2C), 122.77, 125.80, 127.37 (2C), 128.74, 130.67, 137.67, 140.28, 144.66, 147.78, 148.65. Anal. calcd for $C_{18}H_{17}N_5S.0.2HCl$: C, 63.08; H, 5.06; N, 20.43; S, 9.36. found: C, 63.01; H, 5.19; N, 20.43; S, 9.39.

4-(4-Acetoylanilino)-1-methyl-1H-pyrazolo[4,3-c]quinolin-3-amine (Compound 10, HKI-4968)

Yield 60%. Mp.: 272-274° C. (EtOH). $^1$H-NMR (400 MHz, DMSO-d$_6$+TFA-d): δ 2.65 (s, 3H, COCH$_3$), 4.28 (s, 3H, OCH$_3$), 7.62-7.74 (m, 4H, Ar—H), 7.93-7.95 (m, 1H, Ar—H), 8.14-8.17 (m, 2H, Ar—H), 8.39-8.41 (m, 1H, Ar—H). $^{13}$C-NMR (100 MHz, DMSO-d$_6$+TFA-d): δ 26.89, 40.06, 96.94, 113.17, 119.71, 123.61, 123.98 (2C), 126.17, 130.46 (2C), 131.04, 135.22, 135.53, 140.11, 140.97, 147.68, 151.36, 197.17. Anal. calcd for $C_{19}H_{17}N_5O$: C, 68.87, H, 5.17; N, 21.13. found: C, 68.67, H, 5.18; N, 20.95.

4-(2-Hydroxyanilino)-1-methyl-1H-pyrazolo[4,3-c]quinolin-3-amine (Compound 11, HKI-4973)

Yield 64%. Mp.: 233-235° C. (EtOH). $^1$H-NMR (400 MHz, DMSO-d$_6$): δ 4.21 (s, 3H, NCH$_3$), 5.98 (br s, 2H, NH$_2$), 6.91-6.95 (m, 1H, Ar—H), 7.03-7.04 (m, 1H, Ar—H), 7.13-7.14 (m, 1H, Ar—H), 7.24-7.45 (m, 1H, Ar—H), 7.58-7.62 (m, 1H, Ar—H), 7.81-7.83 (m, 2H, Ar—H), 8.26-8.28 (m, 1H, Ar—H). $^{13}$C-NMR (100 MHz, DMSO-d$_6$): δ 39.28, 97.06, 113.06, 116.81 (2C), 119.44 (2C), 122.25, 122.76, 123.97, 124.94, 126.56, 129.68, 139.58, 148.58, 149.38, 150.37. Anal. calcd for $C_{17}H_{15}N_5O.1.0HCl$: C, 59.72; H, 4.72; N, 20.49. found: C, 59.62; H, 5.06, N, 20.30.

4-(3-Hydroxyanilino)-1-methyl-1H-pyrazolo[4,3-c]quinolin-3-amine (Compound 12, HKI-4972)

Yield 70%. Mp.: 190-191° C. (EtOH). $^1$H-NMR (400 MHz, DMSO-d$_6$): δ 4.21 (s, 3H, NCH$_3$), 6.23 (br s, 2H, NH$_2$), 6.66-6.69 (m, 1H, Ar—H), 7.07-7.09 (m, 1H, Ar—H), 7.22-7.26 (m, 2H, Ar—H), 7.45-7.4 (m, 1H, Ar—H), 7.61- 7.65 (m, 1H, Ar—H), 7.83-7.85 (m, 2H, Ar—H), 8.27-8.29 (m, 1H, Ar—H), 9.75 (br s, 1H, OH). $^{13}$C-NMR (100 MHz, DMSO-d$_6$): δ 39.58, 97.14, 110.25, 113.13, 113.59, 122.81, 124.34, 129.83, 130.13, 138.38, 139.77, 148.14, 149.81, 158.31. Anal. calcd for $C_{17}H_{15}N_5O.0.9HCl$: C, 60.36; H, 4.77; N, 20.71. found: C, 59.99, H, 5.06; N, 20.31.

4-(4-Hydroxyanilino)-1-methyl-1H-pyrazolo[4,3-c]quinolin-3-amine (Compound 13, HKI-4971)

Yield 79%. Mp.: 320-322° C. (EtOH). $^1$H-NMR (400 MHz, DMSO-d$_6$): δ 4.20 (s, 3H, NCH$_3$), 6.47 (br s, 2H, NH$_2$), 6.93-6.97 (m, 2H, Ar—H), 7.34-7.37 (m, 2H, Ar—H), 7.48-7.52 (m, 1H, Ar—H), 7.62-7.66 (m, 1H, Ar—H), 7.89-7.91 (m, 1H, Ar—H), 8.27-8.29 (m, 1H, Ar—H), 9.94 (br s, 1H, OH), 11.62 (br s, 1H, NH). $^{13}$C-NMR (100 MHz, DMSO-d$_6$): δ 39.29, 95.29, 112.33, 116.47 (2C), 119.27, 123.10, 125.00, 125.97, 127.36, 130.31, 135.59, 139.17, 148.35, 150.77, 157.17. Anal. calcd for $C_{17}H_{15}N_5O.1.0HCl$: C, 59.72; H, 4.72; N, 20.49. found: C, 59.64, H, 4.85; N, 20.41.

4-(4-Trifluoromethylanilino)-1-methyl-1H-pyrazolo[4,3-c]quinolin-3-amine (Compound 14, HKI-4974)

Yield 59%. Mp.: 219-220° C. (EtOH). $^1$H-NMR (400 MHz, TFA-d): δ 4.28 (s, 3H, NCH$_3$), 7.60-7.63 (m, 1H, Ar—H), 7.72-7.81 (m, 3H, Ar—H), 7.90-7.95 (m, 3H, Ar—H), 8.38-8.40 (m, 1H, Ar—H). Anal. calcd for $C_{18}H_{14}F_3N_5O.1.3HCl$: C, 53.40; H, 3.81; N, 17.30. found: C, 53.00; H, 4.12; N, 17.20.

4-[(3-Amino-1-methyl-1H-pyrazolo[4,3-c]quinolin-4-yl)amino]benzoic acid (Compound 15, HKI-4970)

Yield 68%. Mp.: 325-326° C. (EtOH). $^1$H-NMR (400 MHz, DMSO-d$_6$): δ 4.24 (s, 3H, NCH$_3$), 7.59-7.59 (m, 1H, Ar—H), 7.69-7.79 (m, 3H, Ar—H), 7.87-7.89 (m, 1H, Ar—H), 8.04-8.06 (m, 1H, Ar—H), 8.34-8.37 (m, 1H, Ar—H), 8.27-8.29 (m, 1H, Ar—H). $^{13}$C-NMR (100 MHz, SO-d$_6$): δ 39.29, 97.33, 112.94, 120.22, 122.67, 123.15, 125.46, 127.67, 130.45, 130.91 (2C), 131.16, 136.34, 139.79, 141.47, 147.39, 150.81, 166.82. Anal. calcd for $C_{18}H_{15}N_5O_2.1.0HCl$: C, 58.44; H, 4.36; N, 18.93. found: C, 58.04; H, 4.50; N, 18.79.

2-[(3-amino-1-methyl-1H-pyrazolo[4,3-c]quinolin-4-yl)amino]benzenethiol (Compound 16, HKI-4975)

Yield 42%. Mp.: 235-236° C. (EtOH). $^1$H-NMR (400 MHz, DMSO-d$_6$): δ 3.14 (s, 3H, NCH$_3$), 5.03 (br s, 1H, SH), 6.05 (br s, 1H, NH$_2$), 6.93-6.97 (m, 1H, Ar—H), 6.85-6.87 (m, 1H, Ar—H), 7.02-7.04 (m, 1H, Ar—H), 7.20-7.30 (m, 2H, Ar—H), 7.36-7.41 (m, 1H, Ar—H), 7.81-7.86 (m, 1H, Ar—H). $^{13}$C-NMR (100 MHz, DMSO-d$_6$): δ 35.75, 100.80, 111.46, 115.40, 116.44, 120.82, 121.33, 123.74, 125.82, 131.11, 131.31, 132.51, 140.24, 147.51, 152.11, 153.59, 161.85. Anal. calcd for $C_{17}H_{15}N_5S.0.1HCl$: C, 62.82; H, 4.68; N, 21.55; S, 9.86. found: C, 63.03, H, 4.72; N, 21.55; S, 9.88.

4-(4-Chloroanilino)-1-methyl-1H-pyrazolo[4,3-c]quinolin-3-amine (Compound 17, TCH-30o)

Yield 82%. Mp.: 281-282° C. (EtOH). $^1$H-NMR (400 MHz, DMSO-d$_6$): δ 4.23 (s, 3H, NCH$_3$), 7.53-7.61 (m, 3H, Ar—H), 7.66-7.71 (m, 3H, Ar—H), 7.88-7.90 (m, 1H, Ar—H), 8.33-8.34 (m, 1H, Ar—H), 12.19 (br s, 1H, NH). $^{13}$C-NMR (100 MHz, DMSO-d$_6$): δ 39.77, 96.36, 112.62, 119.49, 123.18, 125.36, 126.43 (2C), 129.74 (2C), 130.46, 130.99, 135.31, 135.70, 139.49, 147.76, 150.97. Anal. calcd for C$_{17}$H$_{14}$ClN$_5$.1.5HCl: C, 53.93; H, 4.13; N, 18.50. found: C, 54.09; H, 4.44; N, 18.53.

4-(4-Methylanilino)-1-methyl-1H-pyrazolo[4,3-c] quinolin-3-amine (Compound 18, TCH-30p)

Yield 85%. Mp.: 253-255° C. (EtOH). $^1$H-NMR (400 MHz, DMSO-d$_6$): δ 2.36 (s, 3H, CH$_3$), 4.20 (s, 3H, NCH$_3$), 6.22 (br s, 2H, NH$_2$), 7.27-7.29 (m, 2H, Ar—H), 7.43-7.47 (m, 1H, Ar—H), 7.559-7.63 (m, 3H, Ar—H), 7.79-7.81 (m, 1H, Ar—H), 8.26-8.28 (m, 1H, Ar—H), 9.72 (br s, 1H, NH). $^{13}$C-NMR (100 MHz, DMSO-d$_6$): δ 20.63, 39.50, 97.08, 113.19, 122.14, 122.67 (2C), 123.14, 124.05, 129.65, 129.78 (2C), 134.30, 135.09, 139.44, 139.76, 148.34, 149.57. Anal. calcd for C$_{18}$H$_{17}$N$_5$.1.1HCl: C, 62.93; H, 5.32; N, 20.39. found: C, 62.80; H, 5.73; N, 20.44.

4-Anilinoisoxazolo[4,5-c]quinolin-3-amine (Compound 19, HKI-4978)

Yield 40%. Mp.: 266-267° C. (Hexane). $^1$H-NMR (400 MHz, DMSO-d$_6$): δ 7.42-7.45 (m, 2H, Ar—H), 7.54-7.71 (m, 6H, Ar—H), 7.96-7.99 (m, 1H, Ar—H), 10.04 (br s, 2H, NH$_2$), 11.47 (br s, 1H, 2H, NH, HCl). $^{13}$C-NMR (100 MHz, DMSO-d$_6$): δ 82.82, 111.73, 123.07, 125.37, 125.61 (2C), 127.63, 129.80 (2C), 132.22, 135.07, 136.29, 148.52, 155.35, 168.52. Anal. calcd for C$_{16}$H$_{12}$N$_4$O.1.1HCl: C, 60.71; H, 4.18; N, 17.70. found: C, 60.94; H, 4.45, N, 17.45.

4-(4-Fluoroanilino)isoxazolo[4,5-c]quinolin-3-amine (Compound 20, HKI-4979)

Yield 67%. Mp.: 271-272° C. (Hexane). $^1$H-NMR (400 MHz, DMSO-d$_6$): δ 7.39-7.44 (m, 3H, Ar—H), 7.60-7.70 (m, 4H, Ar—H), 7.96-7.98 (m, 1H, Ar—H), 7.96-7.99 (m, 1H, Ar—H), 10.02 (br s, 2H, NH$_2$), 11.46 (br s, 1H, 2H, NH, HCl). $^{13}$C-NMR (100 MHz, DMSO-d$_6$): δ 82.69, 111.71, 116.70 (2C, J=22.8 Hz), 118.97, 123.11, 125.39, 128.45 (2C, J=8.3 Hz), 131.16, 132.26, 136.33, 148.87, 155.33, 161.34 (J=242.6 Hz), 168.52. Anal. calcd for C$_{16}$H$_{11}$FN$_4$O.1.0HCl: C, 58.08; H, 3.66; N, 16.94. found: C, 57.97; H, 3.95; N, 16.85.

4-(2-Methoxyanilino)isoxazolo[4,5-c]quinolin-3-amine (Compound 21, HKI-4983)

Yield 40%. Mp.: 261-262° C. (Hexane). $^1$H-NMR (400 MHz, DMSO-d$_6$): δ 3.79 (s, 3H, OCH$_3$), 7.11-7.15 (m, 1H, Ar—H), 7.26-7.28 (m, 1H, Ar—H), 7.40-7.52 (m, 3H, Ar—H), 7.61-7.65 (m, 1H, Ar—H), 7.74-7.76 (m, 1H, Ar—H), 7.96-7.98 (m, 1H, Ar—H), 9.91 (br s, 2H, NH$_2$), 10.99 (br s, 1H, 2H, NH, HCl). $^{13}$C-NMR (100 MHz, DMSO-d$_6$): δ 55.95, 82.11, 111.55, 113.24, 118.81, 121.19, 122.12, 123.25, 125.54, 128.55, 130.19, 132.50, 136.21, 148.49, 154.43, 155.19, 168.64. Anal. calcd for C$_{17}$H$_{14}$N$_4$O$_2$.1.1HCl: C, 58.92; H, 4.40; N, 16.17. found: C, 59.01; H, 4.58; N, 15.92.

4-(3-Methoxyanilino)isoxazolo[4,5-c]quinolin-3-amine (Compound 22, HKI-4982)

Yield 50%. Mp.: 262-263° C. (Hexane). $^1$H-NMR (400 MHz, DMSO-d$_6$): δ 3.80 (s, 3H, OCH$_3$), 6.99-7.02 (m, 1H, Ar—H), 7.26-7.28 (m, 2H, Ar—H), 7.40-7.48 (m, 2H, Ar—H), 7.62-7.66 (m, 1H, Ar—H), 7.71-7.73 (m, 1H, Ar—H), 7.97-7.98 (m, 1H, Ar—H), 10.02 (br s, 2H, NH$_2$), 11.44 (br s, 2H, NH, HCl). $^{13}$C-NMR (100 MHz, DMSO-d$_6$): δ 55.38, 82.50, 111.27, 111.74, 113.43, 117.60, 119.07, 123.05, 125.36, 130.57, 132.23, 136.08, 136.35, 148.48, 155.36, 160.20, 168.51. Anal. calcd for C$_{17}$H$_{14}$N$_4$O$_2$.1.1HCl: C, 58.92; H, 4.40; N, 16.17. found: C, 58.92; H, 4.56; N, 15.85.

4-(4-Methoxyanilino)isoxazolo[4,5-c]quinolin-3-amine (Compound 23, HKI-4981)

Yield 43%. Mp.: 257-259° C. (Hexane). $^1$H-NMR (400 MHz, DMSO-d$_6$): δ 3.84 (s, 3H, OCH$_3$), 7.10-7.13 (m, 2H, Ar—H), 7.38-7.48 (m, 3H, Ar—H), 7.60-7.63 (m, 1H, Ar—H), 7.70-7.72 (m, 1H, Ar—H), 7.95-7.96 (m, 1H, Ar—H), 9.98 (br s, 2H, NH$_2$), 11.17 (br s, 1H, NH), 11.32 (br s, 1H, HCl). $^{13}$C-NMR (100 MHz, DMSO-d$_6$): δ 55.45, 82.38, 111.61, 115.06 (2C), 118.97, 123.05, 125.19, 127.13, 127.66 (2C), 132.17, 136.42, 148.83, 155.31, 158.81, 168.42. Anal. calcd for C$_{17}$H$_{14}$N$_4$O$_2$.1.1HCl: C, 58.92; H, 4.40; N, 16.17. found: C, 58.83; H, 4.49, N, 16.01.

4-(3,4,5-Trimethoxyanilino)isoxazolo[4,5-c]quinolin-3-amine (Compound 24, HKI-4980)

Yield 63%. Mp.: 264-266° C. (Hexane). $^1$H-NMR (400 MHz, DMSO-d$_6$): δ 3.74 (s, 3H, OCH$_3$), 3.79 (m, 6H, OCH$_3$), 6.95 (s, 2H, Ar—H), 7.42-7.44 (m, 1H, Ar—H), 7.62-7.67 (m, 1H, Ar—H), 7.76-7.78 (m, 1H, Ar—H), 7.96-7.99 (m, 1H, Ar—H), 10.02 (br s, 2H, NH$_2$), 11.34 (br s, 1H, NH), 11.44 (br s, 1H, HCl). $^{13}$C-NMR (100 MHz, DMSO-d$_6$): δ 56.12 (2C), 60.01, 82.50, 103.75 (2C), 111.62, 119.01, 123.03, 125.33, 130.14, 132.26, 136.27, 136.87, 148.50, 153.55 (2C), 155.31, 168.47. Anal. calcd for C$_{19}$H$_{18}$N$_4$O$_4$.1.2HCl: C, 55.64; H, 4.72; N, 13.66. found: C, 55.65; H, 5.01; N, 13.51.

4-(4-Methylthioanilino)isoxazolo[4,5-c]quinolin-3-amine (Compound 25, HKI-4984)

Yield 42%. Mp.: 246-247° C. (Hexane). $^1$H-NMR (400 MHz, DMSO-d$_6$): δ 2.55 (s, 3H, SCH$_3$), 7.39-7.52 (m, 5H, Ar—H), 7.61-7.69 (m, 3H, Ar—H), 7.95-7.97 (m, 1H, Ar—H), 10.02 (br s, 2H, NH$_2$), 11.39 (br s, 2H, NH, HCl). $^{13}$C-NMR (100 MHz, DMSO-d$_6$): δ 14.67, 82.70, 111.69, 119.03, 123.04, 125.25, 126.35 (2C), 126.87 (2C), 131.69, 132.16, 136.44, 137.79, 148.55, 155.33, 168.43. Anal. calcd for C$_{17}$H$_{14}$N$_4$OS.1.1HCl: C, 56.33; H, 4.20, N, 15.46; S, 8.85. found: C, 56.21; H, 4.22; N, 15.34; S, 8.88.

4-(3-Acetoylanilino)isoxazolo[4,5-c]quinolin-3-amine (Compound 26, HKI-4986)

Yield 40%. Mp.: 249-250° C. (Hexane). $^1$H-NMR (400 MHz, DMSO-d$_6$): δ 2.62 (s, 3H, COCH$_3$), 7.36 (m, 1H, Ar—H), 7.60-7.65 (m, 3H, Ar—H), 7.89-7.96 (m, 3H, Ar—H), 8.25 (m, 1H, Ar—H), 9.61 (br s, 2H, NH$_2$), 10.94 (br s, 1H, NH), 11.27 (br s, 1H, HCl). $^{13}$C-NMR (100 MHz, DMSO-d$_6$): δ 26.89, 112.30, 122.96 (2C), 124.10, 124.63, 125.77, 128.83, 129.84, 131.92, 137.90, 148.66, 156.13, 167.86, 197.60. Anal. calcd for C$_{18}$H$_{14}$N$_4$O$_2$.1.2HCl: C, 59.69, H, 4.23; N, 15.47. found: C, 59.50; H, 4.62; N, 15.19.

4-(4-Acetoylanilino)isoxazolo[4,5-c]quinolin-3-amine (Compound 27, HKI-4987)

Yield 50%. Mp.: 255-257° C. (Hexane). $^1$H-NMR (400 MHz, DMSO-d$_6$): δ 2.60 (s, 3H, COCH$_3$), 7.36 (m, 1H, Ar—H), 7.60 (m, 2H, Ar—H), 7.79-7.80 (m, 2H, Ar—H), 7.94-7.96 (m, 1H, Ar—H), 8.04-8.06 (m, 1H, Ar—H), 9.45 (br s, 2H, NH$_2$), 10.48 (br s, 1H, NH), 11.83 (br s, 1H, HCl). $^{13}$C-NMR (100 MHz, DMSO-d$_6$): δ 26.67, 84.16, 112.45, 121.48, 122.95 (2C), 123.33, 124.81, 125.15, 129.63 (2C), 130.57, 131.87, 133.32, 148.15, 156.25, 167.76, 196.85. Anal. calcd for C$_{18}$H$_{14}$N$_4$O$_2$.1.3HCl: C, 59.09; H, 4.22; N, 15.31. found: C, 59.20; H, 4.58, N, 14.96.

4-(2-Hydroxyanilino)isoxazolo[4,5-c]quinolin-3-amine (Compound 28, HKI-4990)

Yield 42%. Mp.: 240-241° C. (Hexane). $^1$H-NMR (400 MHz, DMSO-d$_6$): δ 6.87-6.96 (m, 2H, Ar—H), 7.10 (m, 1H, Ar—H), 7.21 (m, 1H, Ar—H), 7.34-7.36 (m, 2H, Ar—H), 7.50 (m, 1H, Ar—H), 7.88 (m, 1H, Ar—H), 8.46 (br s, 1H, NH), 8.78 (br s, 2H, NH$_2$), 11.42 (br s, 1H, OH). $^{13}$C-NMR (100 MHz, DMSO-d$_6$): δ 83.79, 112.90, 119.13, 122.78, 123.03, 124.31, 124.92, 126.09, 128.00, 131.36 (2C), 145.30, 149.84, 150.29, 157.64, 166.34. Anal. calcd for C$_{16}$H$_{12}$N$_4$O$_2$.0.7HCl: C, 60.45; H, 4.03; N, 17.62. found: C, 60.34; H, 4.45; N, 17.52.

4-(4-Hydroxyanilino)isoxazolo[4,5-c]quinolin-3-amine (Compound 29, HKI-4988)

Yield 45%. Mp.: 236-237° C. (Hexane). $^1$H-NMR (400 MHz, DMSO-d$_6$): δ 6.80-6.85 (m, 2H, Ar—H), 7.19-7.23 (m, 1H, Ar—H), 7.44-7.52 (m, 4H, Ar—H), 7.86-7.88 (m, 1H, Ar—H), 8.88 (br s, 2H, NH$_2$), 9.43 (br s, 1H, NH), 10.84 (br s, 1H, OH). $^{13}$C-NMR (100 MHz, DMSO-d$_6$): δ 83.55, 112.63, 113.98, 115.39 (2C), 116.15, 122.67 (2C), 122.98, 125.34, 127.16, 131.27, 149.09, 154.57, 157.10, 166.70. Anal. calcd for C$_{16}$H$_{12}$N$_4$O$_2$.1.9HCl: C, 58.84; H, 4.88, N, 17.16. found: C, 58.74; H, 4.59; N, 17.01.

4-(4-Trifluoromethylanilino)isoxazolo[4,5-c]quinolin-3-amine (Compound 30, HKI-4991)

Yield 42%. Mp.: 227-229° C. (Hexane). $^1$H-NMR (400 MHz, DMSO-d$_6$): δ 7.34 (m, 1H, Ar—H), 7.57 (m, 2H, Ar—H), 7.81-7.93 (m, 3H, Ar—H), 7.93-7.94 (m, 2H, Ar—H), 9.26 (br s, 2H, NH$_2$), 10.16 (br s, 1H, NH), 11.65 (br s, 1H, OH). Anal. calcd for C$_{17}$H$_{11}$F$_3$N$_4$O.0.4HCl: C, 56.88; H, 3.20; N, 15.61. found: C, 56.59; H, 3.34; N, 15.35.

4-[(3-aminoisoxazolo[4,5-c]quinolin-4-yl)amino]benzoic acid (Compound 31, HKI-4985)

Yield 58%. Mp.: 308-310° C. (Hexane). $^1$H-NMR (400 MHz, DMSO-d$_6$): δ 7.44-7.46 (m, 1H, Ar—H), 7.61-7.72 (m, 4H, Ar—H), 7.98-8.09 (m, 3H, Ar—H), 10.05 (br s, 2H, NH$_2$), 11.62 (br s, 1H, NH), 11.80 (br s, 1H, HCl), 13.01 (br s, 1H, COOH). $^{13}$C-NMR (100 MHz, DMSO-d$_6$): δ 83.57, 111.94, 119.23, 123.12, 124.74, 125.61, 129.03, 130.84 (2C), 131.16, 132.29, 136.40, 139.78, 148.40, 155.43, 166.75, 168.60. Anal. calcd for C$_{17}$H$_{12}$N$_4$O$_3$.1.4HCl: C, 54.96; H, 3.64; N, 15.08. found: C, 54.97; H, 3.95; N, 15.303.

4-(4-Chloroanilino)isoxazolo[4,5-c]quinolin-3-amine (Compound 32, TCH-30q)

Yield 75%. Mp.: 268-269° C. (Hexane). $^1$H-NMR (400 MHz, DMSO-d$_6$): δ 7.41-7.46 (m, 1H, Ar—H), 7.59-7.69 (m, 6H, Ar—H), 7.97-7.99 (m, 1H, Ar—H), 9.94 (br s, 2H, NH$_2$), 11.31 (br s, 2H, NH, HCl). $^{13}$C-NMR (100 MHz, DMSO-d$_6$): δ 83.09, 111.86, 119.17, 123.25, 125.67, 127.79 (2C), 129.29 (2C), 132.22, 132.45, 134.15, 136.45, 148.82, 155.48, 168.68. Anal. calcd for C$_{16}$H$_{11}$ClN$_4$O.1.0HCl: C, 55.33; H, 3.49; N, 16.140. found: C, 55.37; H, 3.45; N, 16.24.

4-(4-Methylanilino)isoxazolo[4,5-c]quinolin-3-amine (Compound 33, TCH-30r)

Yield 80%. Mp.: 173-175° C. (Hexane). $^1$H-NMR (400 MHz, DMSO-d$_6$): δ 2.40 (s, 3H, CH$_3$), 7.37-7.45 (m, 5H, Ar—H), 7.61-7.65 (m, 1H, Ar—H), 7.70-7.72 (m, 1H, Ar—H), 7.95-7.98 (m, 1H, Ar—H), 9.92 (br s, 2H, NH$_2$), 11.20 (br s, 2H, NH, HCl). $^{13}$C-NMR (100 MHz, DMSO-d$_6$): δ 20.88, 82.71, 111.75, 119.14, 123.20, 125.50, 125.92 (2C), 130.52 (2C), 132.20, 132.40, 136.42, 137.57, 148.78, 155.44, 168.63. Anal. calcd for C$_{17}$H$_{14}$N$_4$O.1.1HCl: C, 61.78, H, 4.61; N, 16.96. found: C, 61.63; H, 4.62; N, 16.97.

1.2 Characterization of the Compound of Example 1

1.2.1 Compound of Formula (I) Suppresses O$_2$$^{•−}$ Production and Elastase Release in Human Neutrophils In this example, inhibitory effects of compound of Example 1 (i.e., compound of formula (I)) on superoxide anion production and elastase release in human neutrophils were investigated, and results are summarized in Table 2.

TABLE 2

Effects of compound of example 1 on superoxide anion generation and elastase release in FMLP/CB-induced human neutrophils.

| | Compound | Superoxide Anion | | Elastase Release | |
|---|---|---|---|---|---|
| | | IC$_{50}$ (μM)$^a$ | Inhibition % | IC$_{50}$ (μM)$^a$ | Inhibition % |
| 3 | HKI-4961 | 2.39 ± 0.63 | 93.92 ± 6.32*** | 4.09 ± 1.02 | 80.45 ± 2.57*** |
| 4 | HKI-4962 | 1.44 ± 0.22 | 91.16 ± 4.43*** | 5.50 ± 1.50 | 68.04 ± 6.80*** |
| 5 | HKI-4966 | 1.37 ± 0.08 | 90.13 ± 3.38*** | 4.65 ± 2.57 | 66.02 ± 6.51*** |
| 6 | HKI-4965 | >10 | 27.54 ± 5.47** | >10 | 33.36 ± 6.04** |
| 7 | HKI-4964 | 0.51 ± 0.17 | 99.26 ± 1.51*** | 3.77 ± 0.71 | 96.67 ± 6.56*** |
| 8 | HKI-4963 | 0.80 ± 0.09 | 98.19 ± 2.41*** | 3.25 ± 0.08 | 89.77 ± 6.51*** |
| 9 | HKI-4967 | >10 | 47.72 ± 3.32*** | >10 | 20.84 ± 3.75** |
| 10 | HKI-4968 | 1.58 ± 0.16 | 85.10 ± 1.66*** | 4.63 ± 1.10 | 57.17 ± 7.34*** |
| 11 | HKI-4973 | 0.73 ± 0.23 | 93.51 ± 1.75*** | 2.24 ± 0.91 | 101.39 ± 4.50*** |
| 12 | HKI-4972 | 1.89 ± 0.69 | 93.17 ± 3.66*** | 4.62 ± 1.74 | 94.36 ± 8.34*** |
| 13 | HKI-4971 | 0.00369 ± 0.00174 | 88.13 ± 1.19*** | 0.03210 ± 0.01740 | 104.56 ± 2.53*** |
| 14 | HKI-4974 | 4.56 ± 0.83 | 63.09 ± 2.51*** | >10 | 37.61 ± 6.22** |

TABLE 2-continued

Effects of compound of example 1 on superoxide anion generation and elastase release in FMLP/CB-induced human neutrophils.

| | Compound | Superoxide Anion | | Elastase Release | |
|---|---|---|---|---|---|
| | | IC$_{50}$ (μM)$^a$ | Inhibition % | IC$_{50}$ (μM)$^a$ | Inhibition % |
| 15 | HKI-4970 | 1.83 ± 0.17 | 82.93 ± 2.86*** | 3.68 ± 0.42 | 79.42 ± 1.91*** |
| 16 | HKI-4975 | >10 | 4.05 ± 2.95 | >10 | −3.34 ± 1.78 |
| 17 | TCH-30p | 3.49 ± 1.25 | 82.78 ± 5.36*** | 5.28 ± 0.66 | 75.78 ± 6.64*** |
| 18 | TCH-30o | 5.21 ± 1.90 | 69.71 ± 7.05*** | >10 | 39.66 ± 3.83*** |
| 19 | HKI-4978 | >10 | 43.73 ± 6.43*** | >10 | 5.81 ± 5.22 |
| 20 | HKI-4979 | 6.16 ± 1.18 | 63.22 ± 7.76* | >10 | 10.69 ± 4.00* |
| 21 | HKI-4983 | >10 | 32.68 ± 4.92** | >10 | −8.32 ± 2.23* |
| 22 | HKI-4982 | 6.53 ± 0.90 | 69.18 ± 3.14*** | >10 | −3.61 ± 0.98* |
| 23 | HKI-4981 | 8.59 ± 0.29 | 59.08 ± 2.03*** | >10 | −9.67 ± 3.44* |
| 24 | HKI-4980 | >10 | 17.10 ± 3.77** | >10 | −10.55 ± 3.81* |
| 25 | HKI-4984 | — | enhanced | >10 | 18.10 ± 3.97** |
| 26 | HKI-4986 | 2.88 ± 0.27 | 76.17 ± 4.68*** | >10 | −4.55 ± 5.83 |
| 27 | HKI-4987 | >10 | 37.41 ± 5.43*** | >10 | −9.53 ± 5.26 |
| 28 | HKI-4990 | 4.54 ± 1.18 | 91.04 ± 1.69*** | 5.77 ± 1.14 | 77.57 ± 4.52*** |
| 29 | HKI-4988 | 0.65 ± 0.20 | 91.10 ± 0.38*** | >10 | 29.85 ± 6.66** |
| 30 | HKI-4991 | — | enhanced | 6.23 ± 0.52 | 81.50 ± 6.97*** |
| 31 | HKI-4985 | >10 | 7.44 ± 4.23 | >10 | −1.40 ± 3.53 |
| 32 | TCH-30q | >10 | 38.65 ± 2.30*** | >10 | 3.69 ± 3.42 |
| 33 | TCH-30r | — | enhanced | 7.24 ± 0.72 | 67.96 ± 5.23*** |

Percentage of inhibition (Inh %) at 10 μM concentration.
Results are presented as mean ± S.E.M. (n = 3-5). *P < 0.05, P < 0.01, *P < 0.001 compared with the control value.
$^a$Concentration necessary for 50 % inhibition (IC$_{50}$).

As evident from Table 2, most compounds, except compounds 6, 9, 16, 19, 21, 24, 25, 27, 30, 31, 32, and 33, were capable of suppressing the superoxide anion generation (IC$_{50}$ ranged from about 4 nM to 8.6 μM) and elastase released (IC$_{50}$ ranged from about 32 nM to 7.2 μM) from the neutrophils in response to fMLF. Among them, compound 13 (HKI-4971) appeared to be most potent, with IC$_{50}$ being about 3.7±1.7 nM for suppressing the superoxide anion generation, and 32±17 nM for suppressing elastase release. Accordingly, HKI-4971 was chosen for further evaluation on its biological activities in Examples 2 and 3.

Example 2 HKI-4971 Suppresses the Development of Imiquimod-Induced Psoriasis

Figure 2:
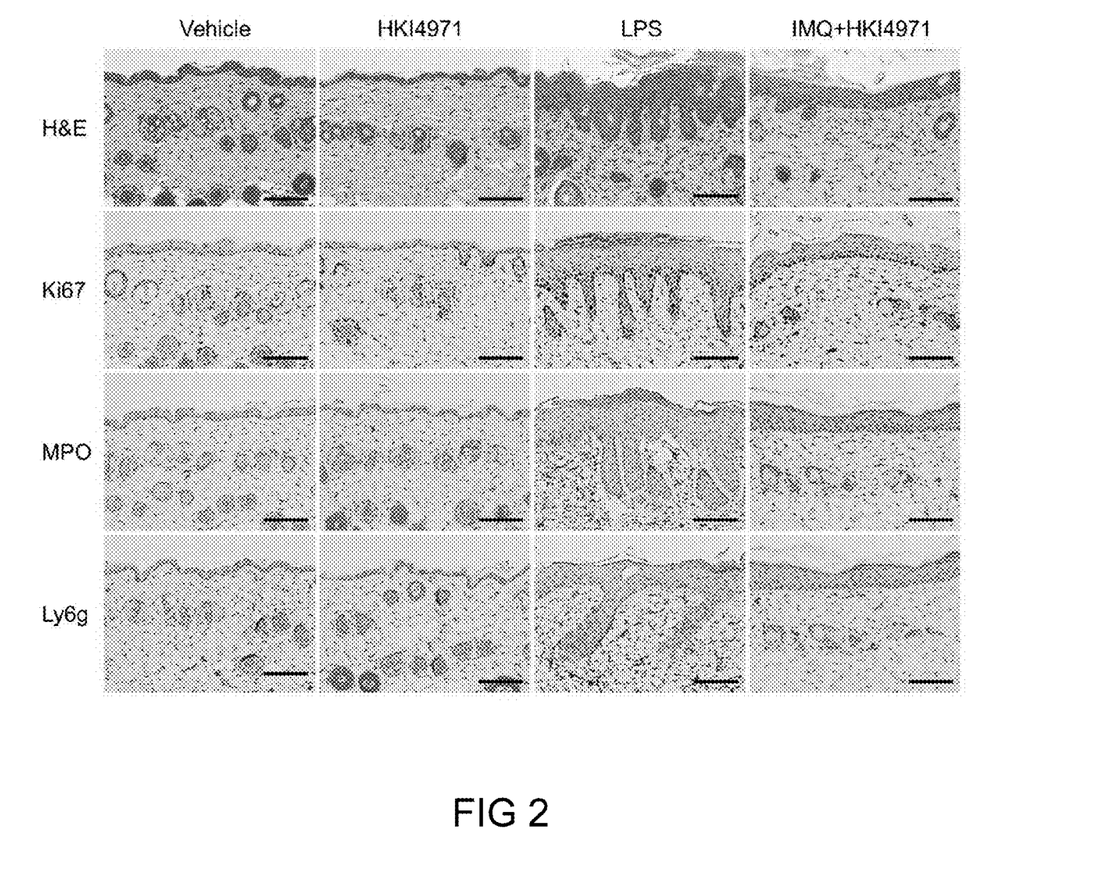
FIG. 2 illustrate the H&E staining and immunohistochemistry staining of the skin taken from psoriasis mice treated with compound HKI-4971 in according to one embodiment of the present disclosure. Scale bars=100 μm.
Figure 3:
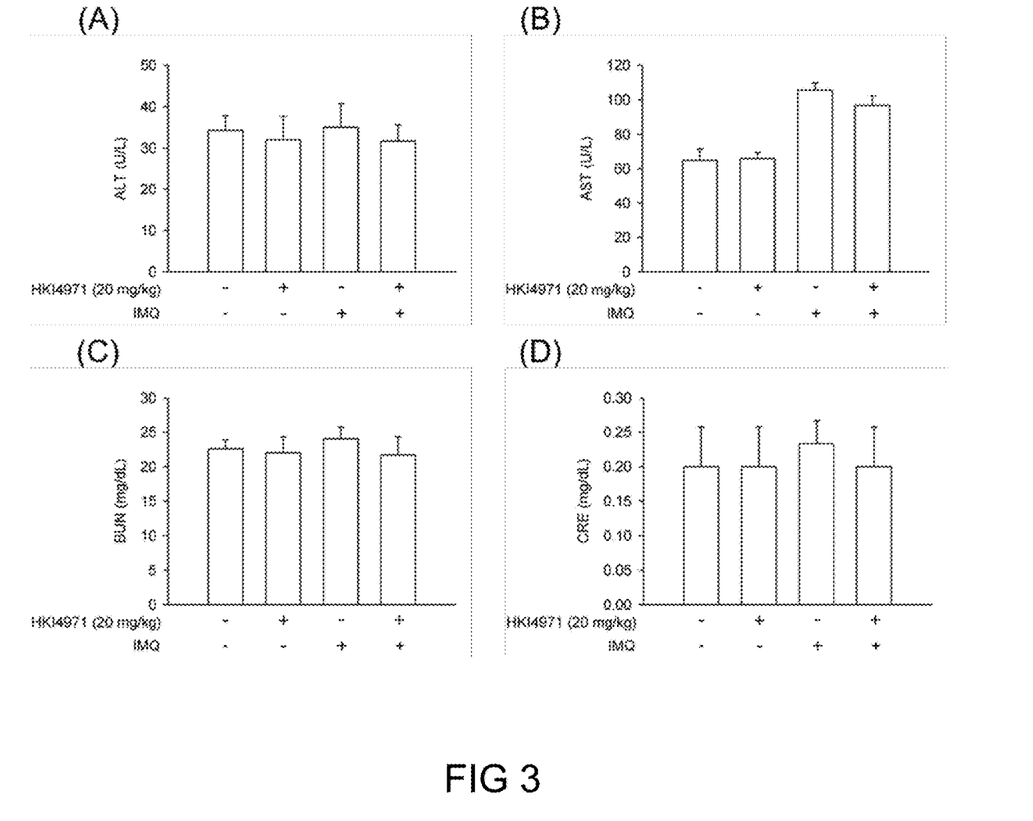
FIG. 3 illustrates the effect of HK-4971 on liver and kidney functions in imiquimod-induced mice. (A) Alanine aminotransferase, (B) aspartate transaminase, (C) blood urine nitrogen, and (D) creatinine were measured. Data are expressed as the mean±S.E.M (n=3).

In this example, the effect of HKI-4971 (or compound 13) on the development of psoriasis was investigated using the well-established psoriasis animal model, in which imiquimod (IMQ) was used to induce psoriasis-like skin inflammation. Briefly, BALB/c mice are pre-treated by intraperitoneal injection of HKI-4971 (20 mg/kg) for 30 min before 5% IMQ cream was topically administered onto the back of the mice every day for 7 days. Then, skin samples taken from these animals were subjected to microscopy examination and immunohistochemistry staining, while blood samples were subjected to analysis for liver and kidney functions. Results are depicted in FIGS. 1 to 3.

Figure 1:
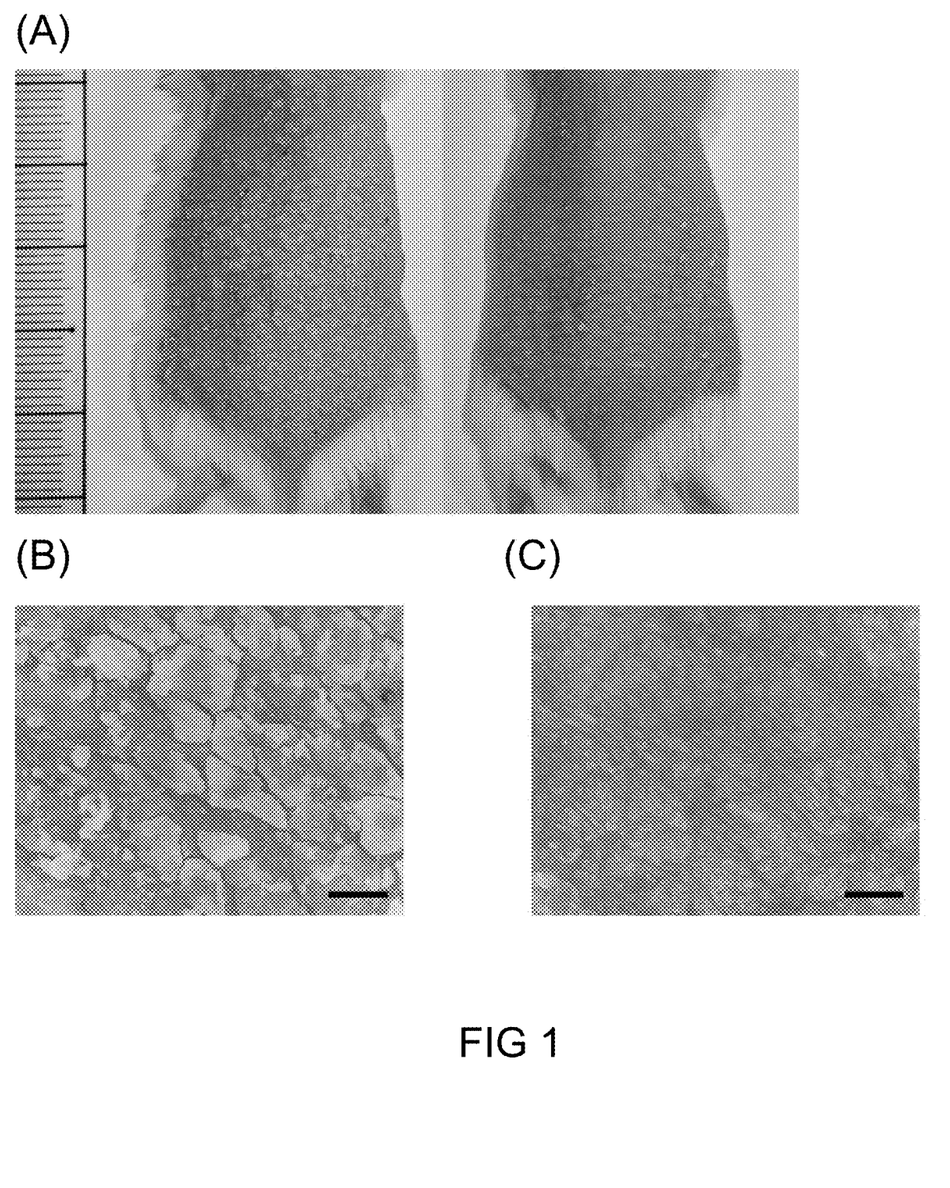

FIG. 1(A) is a photograph taken from one representative mouse treated with IMQ (left), and IMQ+HKI-4971 (right); while photographs in FIGS. 1(B) and 1(C) respectively illustrating microscopic presentation of the skins taken from the control IMQ-treated mouse, and the mouse treated with IMQ+HKI-4971. Immunostaining of skin samples taken from these animals confirmed that the markers for cell proliferation (i.e., ki-67) and for neutrophils (i.e., Ly6g and MPO) were reduced by HKI-4971 (FIG. 2). Thus, it is clear that HKI-4971 may reduce the severity or progression of IMQ-induced psoriasis in the tested animals.

Blood samples taken from IMQ- or IMQ+HKI-4971 treated animals were analyzed for the levels of alanine aminotransferase and aspartate transaminase, which were used as indicators for assessing liver function; and the levels of blood urine nitrogen (BUN) and creatinine (CRE), which were used as indicators for assessing the kidney function. Results are illustrated in FIG. 3. As evident from the data presented in FIG. 3, treatment of IMQ or HKI-4971, either alone or in combination, did not result in significant damage to the functions of liver or kidney.

Taken together, the data confirmed that HK-4971 manifested a protective effect on IMQ-induced psoriasis, thus it may be used as a medicament to treat psoriasis or skin-inflammatory diseases, which often develops after a variety of insults, including but not limiting to, bacterial infection, trauma, autoimmune disorder, and allergy.

Example 3 HKI-497 Modulates LPS-Induced ALI

In this example, the Gram-negative bacterial endotoxin LPS induced ALI in mice was employed to mimic ARDS in human, and the effect of HKI-4971 was evaluated. Briefly, BALB/c mice were pre-treated by intravenous injection of compound HKI-4971 (20 mg/Kg) for 1 hr, and then challenged with intratracheal injection of LPS (2 mg/Kg) for 5 hrs. The level of MPO activity and the markers for neutrophils (Ly6g and MPO) in lung tissues were taken as indications of lung injury. Results are depicted in FIG. 4.

Figure 4:
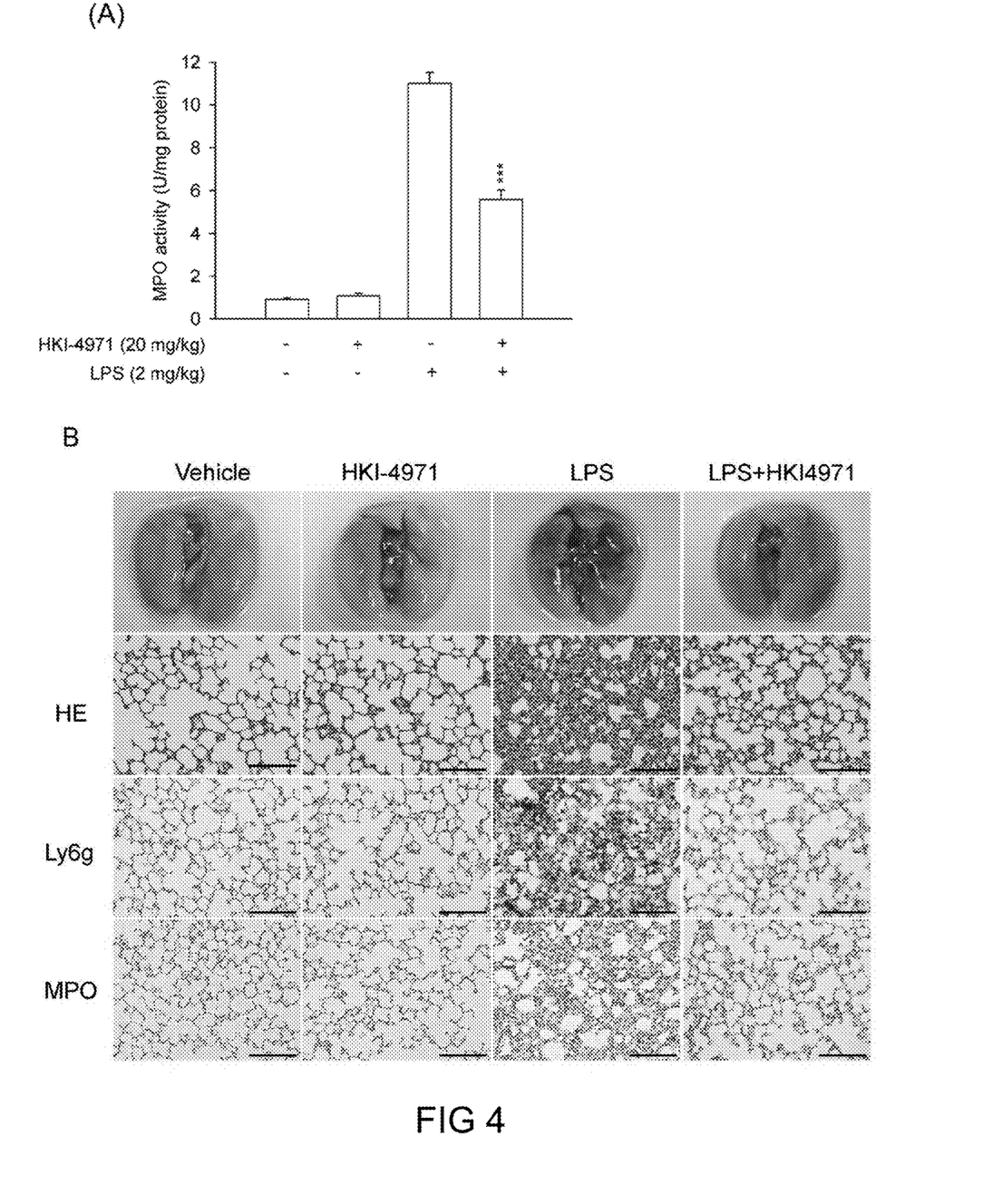
FIG. 4 illustrates the effect of HK-4971 on acute lung injury (ALI) induced by lipopolysaccharide (LPS) in mice. (A) Myeloperoxidase (MPO) activity of lung tissues. (B) Upper panel: Representative photos of lungs. Down panel: Photomicrograph of H&E and immunohistochemistry stained lung sections by light microscopy. Data are expressed as mean±S.E.M. (n=3). Scale bar=100 μm. ***$P<0.01$

As FIG. 4(A) depicted, LPS evoked a surge in MPO activity in lung tissues, an indication of inflammatory cells in lung tissue, which was suppressed by the administration of HKI-4971. FIG. 4(B) are representative photographs of lung sections staining by H&E and the markers for neutrophils viewed under light microscopy. It is evident that HKI-4971 significantly alleviated LPS-induced neutrophil infiltration and lung injury.

Taken together, the data confirmed that HK-4971 manifested a protective effect on LPS-induced lung injury, thus it may be used as a medicament to treat ALI or ARDS, which often develops after a variety of insults, including but not limiting to, sepsis, trauma, and pneumonia.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A compound of formula (I), a salt, or a solvate thereof:

(I)

wherein,

X is N or O;

$R_1$ is alkyl or nil, in which $R_1$ is nil when X is O, and $R_1$ is alkyl when X is N;

$R_2$, $R_3$, $R_4$, and $R_5$ are independently H, hydroxyl, sulfhydryl, halogen, alkyl, haloalkyl, —$OR_6$, —$SR_6$, —(C=O)$R_6$, or —COOH; and $R_6$ is alkyl or haloalykl.

2. The compound of claim 1, wherein X is N; $R_1$ is methyl; $R_2$, $R_3$, and $R_5$ are independently H; and $R_4$ is hydroxyl.

3. A pharmaceutical composition comprising a compound of formula (I), a salt, or a solvent thereof, (I)

wherein,

X is N or O;

$R_1$ is alkyl or nil, in which $R_1$ is nil when X is O, and $R_1$ is alkyl when X is N;

$R_2$, $R_3$, $R_4$, and $R_5$ are independently H, hydroxyl, sulfhydryl, halogen, alkyl, haloalkyl, —$OR_6$, —$SR_6$, —(C=O)$R_6$, or —COOH; and $R_6$ is alkyl or haloalkyl; and a pharmaceutically acceptable excipient.

4. The pharmaceutical composition of claim 3, wherein in the compound of formula (I), X is N; $R_1$ is methyl; $R_2$, $R_3$, and $R_5$ are independently H; and $R_4$ is hydroxyl.

5. A method for treating an inflammatory disease and/or disorder in a subject comprising administering to the subject a therapeutically effective amount of a compound of formula (I), a salt, or a solvate thereof, (I)

wherein,

X is N or O;

$R_1$ is alkyl or nil, in which $R_1$ is nil when X is P, and $R_1$ is alkyl when X is N;

$R_2$, $R_3$, $R_4$, and $R_5$ are independently H, hydroxyl, sulfhydryl, halogen, alkyl, —$OR_6$, —$SR_6$, —(C=O)$R_6$, or —COOH; and $R_6$ is alkyl optionally substituted with at least one halogen.

6. The method of claim 5, wherein in the compound of formula (I), X is N; $R_1$ is methyl; $R_2$, $R_3$, and $R_5$ are independently H; and $R_4$ is hydroxyl.

7. The method of claim 5, wherein the inflammatory disease and/or disorder is selected from the group consisting of acute respiratory distress syndrome (ARDS), acute lung injury (ALI), chronic Obstructive Pulmonary Disease (COPD), lung fibrosis, liver injury, steatohepatitis, liver fibrosis, ischemia-reperfusion injury, myocardial infarction, shock, stroke, and organ transplantation, vasculitis, systemic lupus erythematosus (SLE), sepsis, systemic inflammatory response syndrome (SIRS), arthritis, psoriasis, atopic dermatitis, and inflammatory skin diseases.

8. The method of claim 7, wherein the inflammatory disease and/or disorder is ALI.

9. The method of claim 7, wherein the inflammatory disease and/or disorder is ARDS.

10. The method of claim 7, wherein the inflammatory disease and/or disorder is psoriasis.

11. The method of claim 5, wherein the compound of formula (I) is administered to the subject in the amount of 0.001-100 mg/Kg.

12. The method of claim 5, wherein the subject is a human.

* * * * *